United States Patent [19]

Brown

[11] Patent Number: 5,868,137

[45] Date of Patent: Feb. 9, 1999

[54] PENIS SUPPORT DEVICE FOR MALES

[76] Inventor: Lester Z. Brown, 351 Circulo San Blas, Rohnert Park, Calif. 94928

[21] Appl. No.: 732,071

[22] Filed: Oct. 16, 1996

[51] Int. Cl.[6] .......................................................... A61F 6/02
[52] U.S. Cl. ............................................... 128/842; 600/39
[58] Field of Search ....................................... 128/842, 844, 128/918; 604/349–353; 600/38, 39

[56] References Cited

U.S. PATENT DOCUMENTS

| 837,993 | 12/1906 | Williams | 600/39 |
|---|---|---|---|
| 3,131,691 | 5/1964 | Scott | 600/39 |
| 4,615,337 | 10/1986 | Allinson | 600/39 |
| 4,893,616 | 1/1990 | Immonen | 600/39 |
| 5,360,390 | 11/1994 | Maanum | 600/39 |

Primary Examiner—Michael A. Brown

[57] ABSTRACT

A penis support device to help provide stiffness to the penis for those men who have trouble getting or maintaining an erection for the purpose of having satisfactory sexual intercourse. The device is made of one piece of semi rigid molded material such as thirty durometer Santoprene. The device is generally tubular in shape, having a slit running the length of the tube. The slit is wider at the head of the top where the penis head resides and narrower along the remainder of the tube. The walls of the tube are thicker at the portion opposite the slit and become progressively thinner until at the slit edge the wall is at its thinnest. The penis support device of the present invention is easily applied to the penis and may be easily rotated about the longitudinal axis of the penis to suit the user. The device of the present invention has smooth walls with not protrusions so that a condom may easily be applied over the device.

4 Claims, 2 Drawing Sheets

PENIS SUPPORT DEVICE FOR MALES

FIELD OF THE INVENTION

The present invention is directed to an improved device for attachment and use with a penis to aid in the act of sexual intercourse. Over fifteen million men in the United States have some difficulty producing and maintaiing an erection of the penis for the purpose of satisfactory sexual intercourse. The device of the present invention acts as a penis support to help those millions of men with the above stated problem better known as impotence.

BACKGROUND OF THE INVENTION

A number of devices have been proposed in the past for treating impotence or for serving as a prosthetic penis. U.S. Pat. Nos. 837,993; 1,216,099; 1,362,398; 3,131,691; 3,495,588; 3,939,827; 4,022,196; 4,206,752; 4,262,662; and 4,429,689 illustrate a variety of approaches to this problem over the past eighty years.

All the previous designs, while providing some degree of effectiveness, have some drawbacks which will be remedied by the present invention. Some past devices have either been bulky or cumbersome to put on requiring straps around the buttox or scrotum. Other devices have not supported the entire penis or have ended up covering the penile opening thereby blocking the ejection of sperm. Others have been unaccomodating to various sized penis's either in diameter or in length. Still others have been difficult to use in combination with a condom. Others are not reusable or are difficult to clean. Still others seek to hold the device on by surrounding the penis with loops thereby making the device difficult to put on and restrictive to a penis of large size. Finally, some of the designs cover the penis in such a way as to make it difficult for the sensitive areas at the head to the penis to be stimulated thereby making ejaculation difficult.

OBJECTS AND SUMMARY OF THE PRESENT INVENTION

It is an object of the present invention to provide an improved penis supporting device which remedies the above problems. Therefore the device of the present invention is streamlined in shape, easy to put on, is made of one flexible molded piece, does not cover the penile opening, requires no straps to stay in place, must be used with a condom, can expand or contract to fit various diameter penis's, can be cut to length to accommodating penis's of various lengths and finally, can be positioned in various angles about the longitudinal axis of the penis thereby providing optimal exposure of the head of the penis for each individual user.

To accomplish the above objectives the penis support device of the present invention is molded in a single piece of thirty shore durometer Santgprene which is a rubber like injection moldable plastic. The device is basically tubular in shape with a longitudinal slit running the length of the device. The device can easily expand and contract radially to accommodate various diameter penis's The slit is widened in the front section to allow ample room for the exposure of the penis head thereby allowing the head to be properly stimulated. The front of the device is tapered in but remains open at the very front to allow for comfortable ejaculation. The edges of the device are all tapered to feather edges for comfort to the user and so as not to interfere with or tear a condom. The device can be worn so that the slit and wider opening at the head portion can be located at the top, side or underside of the penis depending on the preference of the user so that the user may obtain maximum stimulation in a way which he individually prefers. The wall thickness of the sheath is semi-rigid but flexible enough that it can be bent outwardly in a flange like manner about the base of the penis when measuring for the correct length of the device. The excess amount of the sheath can then be cut at its base so that the final length is custom made for the user.

These and other objects of the present invention will be fully described in the drawings and description of drawings shown below.

DETAILED DESCRIPTION OF THE DRAWINGS

Figure 1:
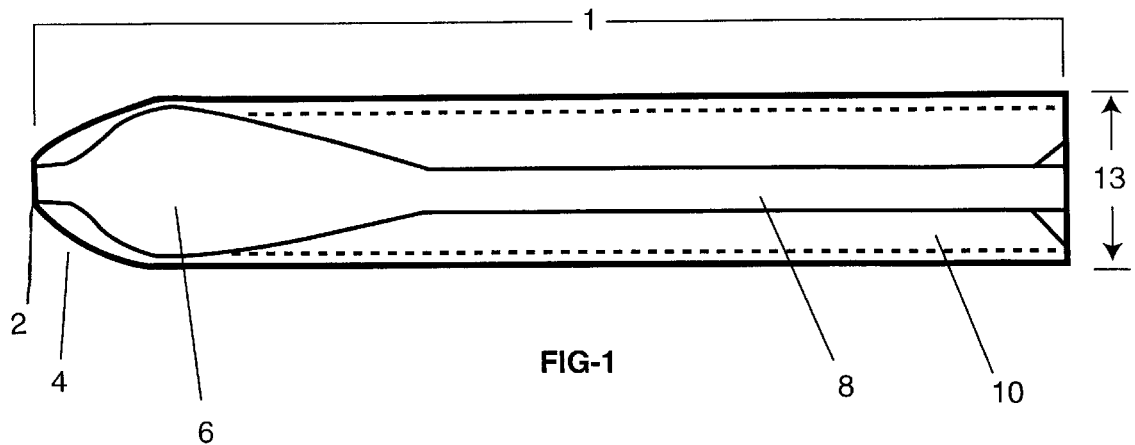
FIG. 1 is a top view of the penis supporting device of the present invention

Referring now to FIG. 1 the overall length of the device 1 of the present invention is about six and three quarters of an inch long and one inch wide 13 before use. The entire assembly is made of semi rigid Santoprene, a rubber like plastic having a durometer of about thirty shore. The Santoprene material is flexible enough that the longitudinal edges of the device may be spread by the user to make installation onto the penis quick and easy. Also because the resting inside diameter of the springy material of the present device is only about seven eighths of an inch, the walls of the device will contract to conform with the diameter of various sizes of penis and remain securely attached while the user covers the device and enclosed penis with a condom. The front tip of the device 4 curves upwardly around part of the head of the penis just enough to secure the device to the head of the penis but not so much as to impede the ability of the head of the penis to be exposed thereby increasing the ability of the head of the penis to be stimulated. Slit 8 is widened at the front 6 to allow for maximum exposure of the head of the penis. Opening 2 at the very tip of the device allows the penile opening to be completely exposed thereby aiding in comfortable ejaculation during intercourse.

Figure 2:
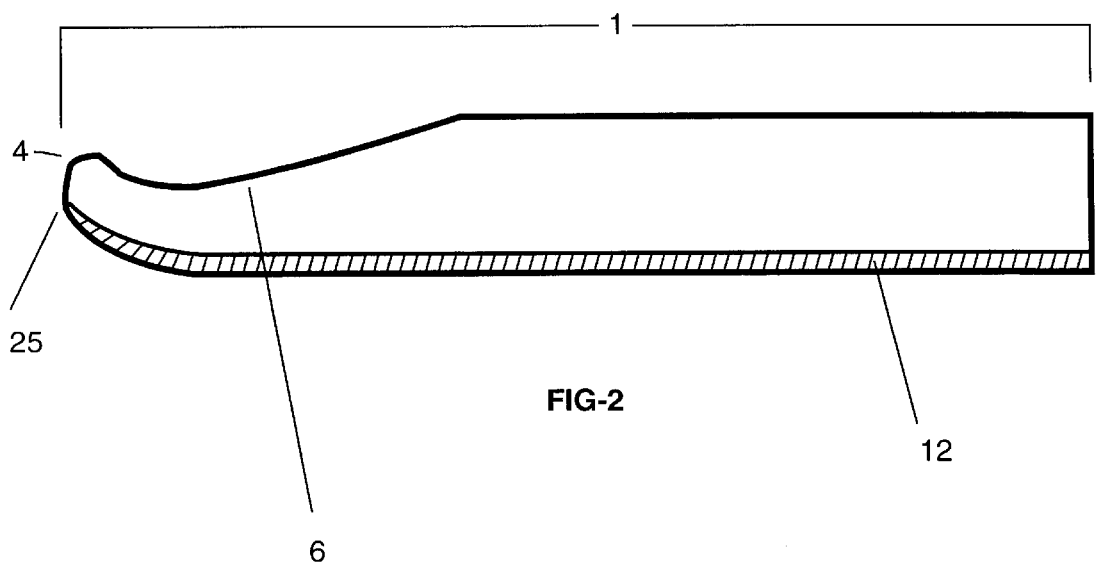
FIG. 2 is a side section view of the penis supporting device of the present invention.

Side section view shown in FIG. 2 shows more clearly that the sheath portion at the front of the device is cut away to allow for more exposure of the penis head. Wall thickness 12 is approximately eighty-five thousandths of an inch and decreases to fifteen thousandths of an inch at the tip 25. Front portion 4 is rounded for comfort and the wall thickness at this portion remains thin, about fifteen thousandths of an inch.

Figure 3:
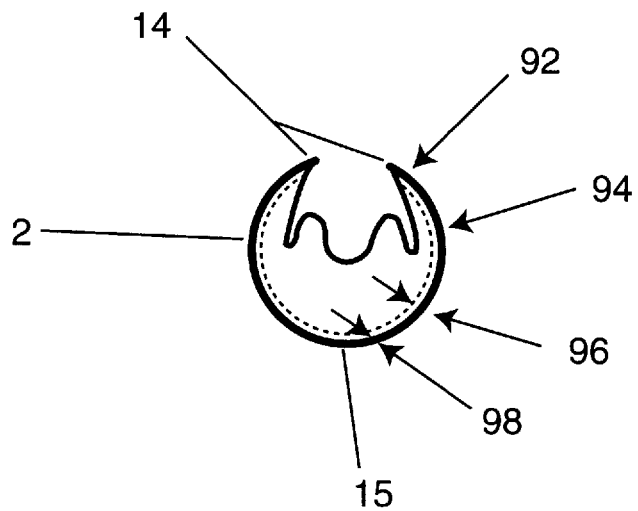
FIG. 3 is a front view to the penis supporting device of the present invention.

FIG. 3 is a front view of the device of the present invention and the dotted line 15 shows that the wall section is thickest at the bottom and becomes progressively tinner at the top. The thickness at 98 is eighty-five thousandths of an inch, at 96 is seventy thousandths of an inch, at 94 is sixty thousandths of an inch, at 92 is thirty-five thousandths of an inch and finally at 14 is fifteen thousandths of an inch.

Figure 4:
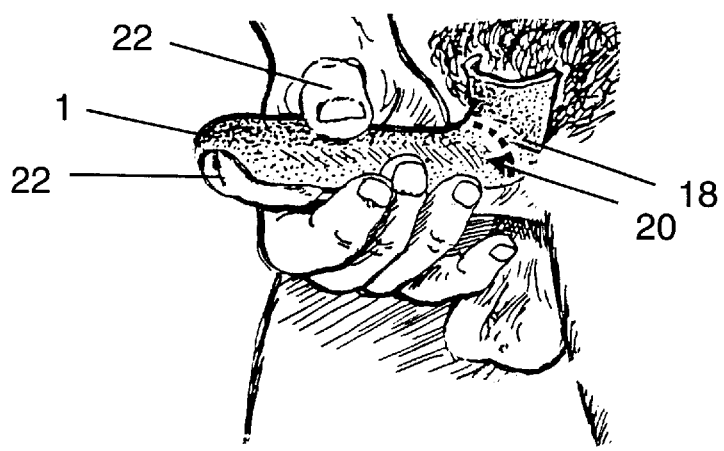
FIG. 4 is a perspective view of a user installing the penis supporting device of the present invention.

FIG. 4 shows a persons hand 22 applying the penis supporting device 1 of the present invention. Notice that the overall length of the device 1 is longer than necessary for the individual pictured so the user can cut the excess portion 18 off with a scissors at dotted line 20 to produce a perfect fit. The user can also rotate the entire assembly 1 about the longitudinal axis of the penis to expose the area of the penis that is most sensitive to stimulation of that particular user. A condom is then rolled over the entire assembly which further causes the device 1 to remain securely in place during sexual intercourse.

While the present invention has been described in connection with what are presently considered to be the most practical and preferred embodiment, it is to be understood that the present invention is not limited to the disclosed embodiment, bet, on the contrary, it is intended to cover various modifications and equivalent arrangements included within the spirit and scope of the appended claims.

I claim:

1. A penis supporting device comprising a single molded, semi-rigid material forming a tubular member, said tubular member adapted to fit a variety of penis of different sizes, said tubular member having a slit along its longitudinal axis, a wall thickness, a head section and a base section, said slit being narrow at said base section and wider at said head section, said tubular member being flexible enough to be expanded during application to the penis and flexible enough to return to fit the side walls of the user's penis in a secure manner, said slit having top edges, said wall thickness of said tubular member being progressively tapered about the radius of said tubular member, wherein said base section of said tubular member is thicker and the top edges of the slit are thinner.

2. The penis supporting device of claim 1, wherein said walls of said tubular member are smooth without protrusions so as to easily accept a condom over the tubular member.

3. The penis supporting device of claim 1, wherein said tubular member may be easily turned about the longitudinal axis of the penis of the user thereby allowing the user to select the ideal radial position for maximum stimulation during sexual intercourse.

4. The penis supporting device of claim 1 wherein material of said tubular member at said base section is thin enough to be cut with a pair of scissors thereby enabling the user to trim the length of said tubular member to correspond to the length of the user's penis.

* * * * *